United States Patent
Shimamoto

(10) Patent No.: US 10,534,168 B2
(45) Date of Patent: Jan. 14, 2020

(54) LIGHT-SCANNING APPARATUS AND LIGHT-SCANNING-APPARATUS CONTROL METHOD

(71) Applicant: OLYMPUS CORPORATION, Tokyo (JP)

(72) Inventor: Atsuyoshi Shimamoto, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 29 days.

(21) Appl. No.: 15/910,071

(22) Filed: Mar. 2, 2018

(65) Prior Publication Data

US 2018/0196250 A1  Jul. 12, 2018

Related U.S. Application Data

(63) Continuation of application No. PCT/JP2015/079864, filed on Oct. 22, 2015.

(51) Int. Cl.
*G02B 23/24* (2006.01)
*H04N 3/30* (2006.01)
(Continued)

(52) U.S. Cl.
CPC ......... *G02B 23/2469* (2013.01); *G02B 23/26* (2013.01); *H04N 3/30* (2013.01);
(Continued)

(58) Field of Classification Search
CPC .... G02B 23/2469; H04N 5/2256; H04N 3/30; A61B 1/00165
(Continued)

(56) References Cited

U.S. PATENT DOCUMENTS 2,852,772 A * 9/1958 Gitzendanner .......... H01Q 3/42
342/371
3,636,250 A * 1/1972 Haeff ................. B23D 57/0061
358/480
(Continued)

FOREIGN PATENT DOCUMENTS

JP 2010-142597 A 7/2010
JP 5190267 B2 4/2013
(Continued)

OTHER PUBLICATIONS

International Search Report dated Jan. 19, 2016 issued in PCT/JP2015/079864.

*Primary Examiner* — Zaihan Jiang
(74) *Attorney, Agent, or Firm* — Scully, Scott, Murphy & Presser, P.C.

(57) ABSTRACT

A light-scanning apparatus according to the present invention is provided with: an optical fiber; a signal-generating portion that generates a driving signal that has a frequency fd different from a resonant frequency fr of the optical fiber; and a driving portion that causes a distal end of the optical fiber to undergo spiral oscillations in accordance with the driving signal, wherein the signal-generating portion generates the driving signal that includes, during one scanning period, a first period in which an amplitude gradually increases from substantially zero to a maximum value and a second period in which the amplitude gradually decreases from the maximum value to substantially zero, and that satisfies conditional expression (1) below. N2 is the number of oscillations of the driving signal in the second period.

{Eq. 1}

$$2 \geq \frac{1}{N2^2} \cdot \frac{12}{\left(\frac{fd}{fr}-0.999\right)^2} \left(\text{when } \frac{fd}{fr} > 1\right) \quad (1)$$

5 Claims, 12 Drawing Sheets

(51) Int. Cl.
  *H04N 5/225*   (2006.01)
  *G02B 23/26*   (2006.01)
  *A61B 1/00*    (2006.01)

(52) U.S. Cl.
  CPC ........ *H04N 5/2256* (2013.01); *A61B 1/00165* (2013.01); *H04N 2005/2255* (2013.01)

(58) Field of Classification Search
  USPC .......................................................... 348/65
  See application file for complete search history.

(56) References Cited

U.S. PATENT DOCUMENTS

| | | | | |
|---|---|---|---|---|
| 6,091,067 | A * | 7/2000 | Drobot | G02B 26/10 |
| | | | | 250/227.11 |
| 6,137,105 | A * | 10/2000 | Drobot | G02B 26/10 |
| | | | | 235/462.33 |
| 6,246,658 | B1 * | 6/2001 | White | G11B 7/128 |
| | | | | 369/112.27 |
| 6,341,118 | B1 * | 1/2002 | Drobot | G11B 7/005 |
| | | | | 369/112.27 |
| 2005/0024701 | A1 * | 2/2005 | Cannon | G02B 26/105 |
| | | | | 359/204.1 |
| 2010/0157037 | A1 | 6/2010 | Iketani et al. | |
| 2012/0033279 | A1 * | 2/2012 | Furukawa | G02B 26/0833 |
| | | | | 359/199.1 |
| 2014/0043086 | A1 * | 2/2014 | Kakinuma | H01L 43/08 |
| | | | | 327/356 |
| 2014/0043614 | A1 * | 2/2014 | Dhayalan | G02B 6/42 |
| | | | | 356/445 |
| 2016/0248310 | A1 * | 8/2016 | Elenga | H02K 33/16 |
| 2016/0324403 | A1 * | 11/2016 | Yeoh | A61B 1/00165 |
| 2016/0373056 | A1 * | 12/2016 | Kumar | H03B 5/06 |

FOREIGN PATENT DOCUMENTS

| | | | |
|---|---|---|---|
| JP | 2015119931 A | * | 12/2013 |
| JP | 2015-119931 A | | 7/2015 |
| JP | 2015119931 A | * | 7/2015 |
| WO | WO 2006/041452 A1 | | 4/2006 |

* cited by examiner

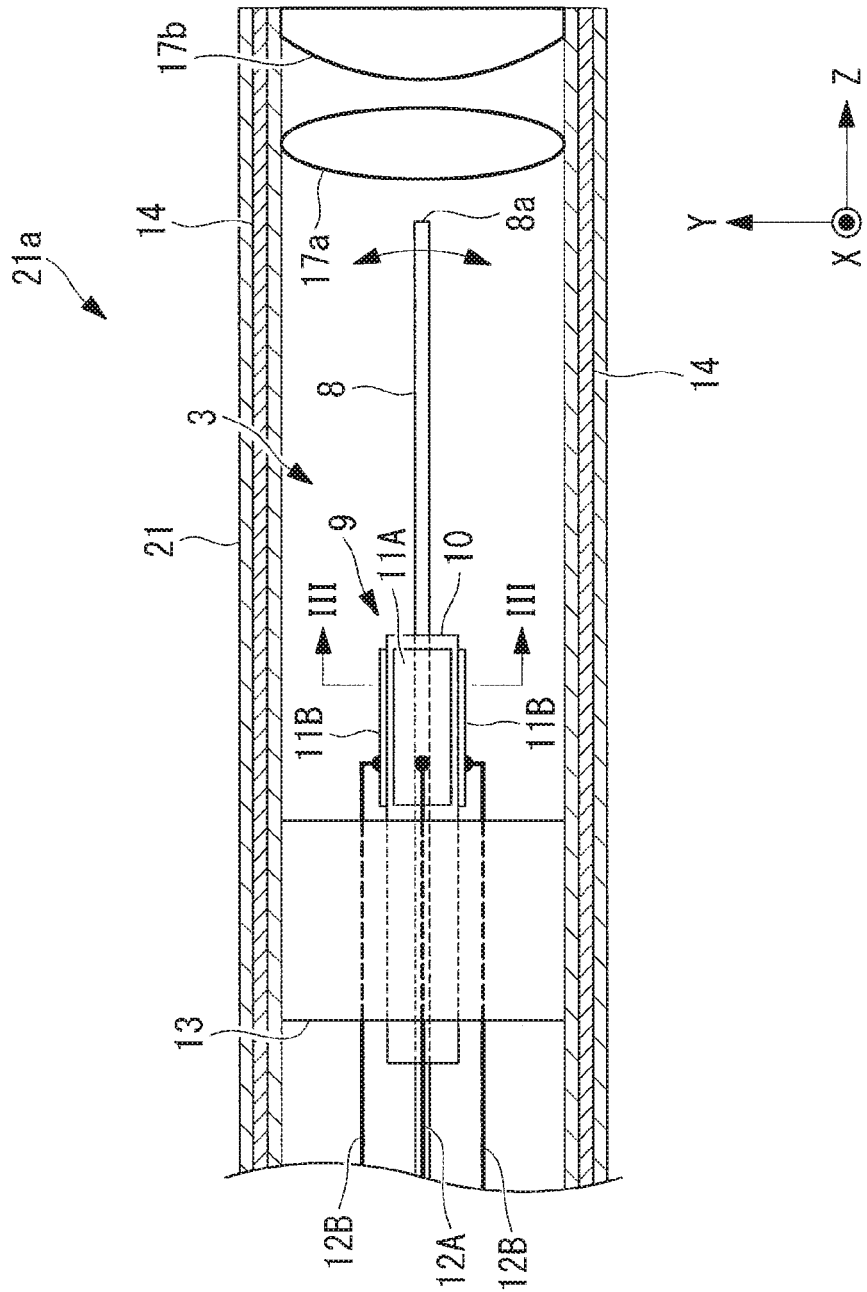

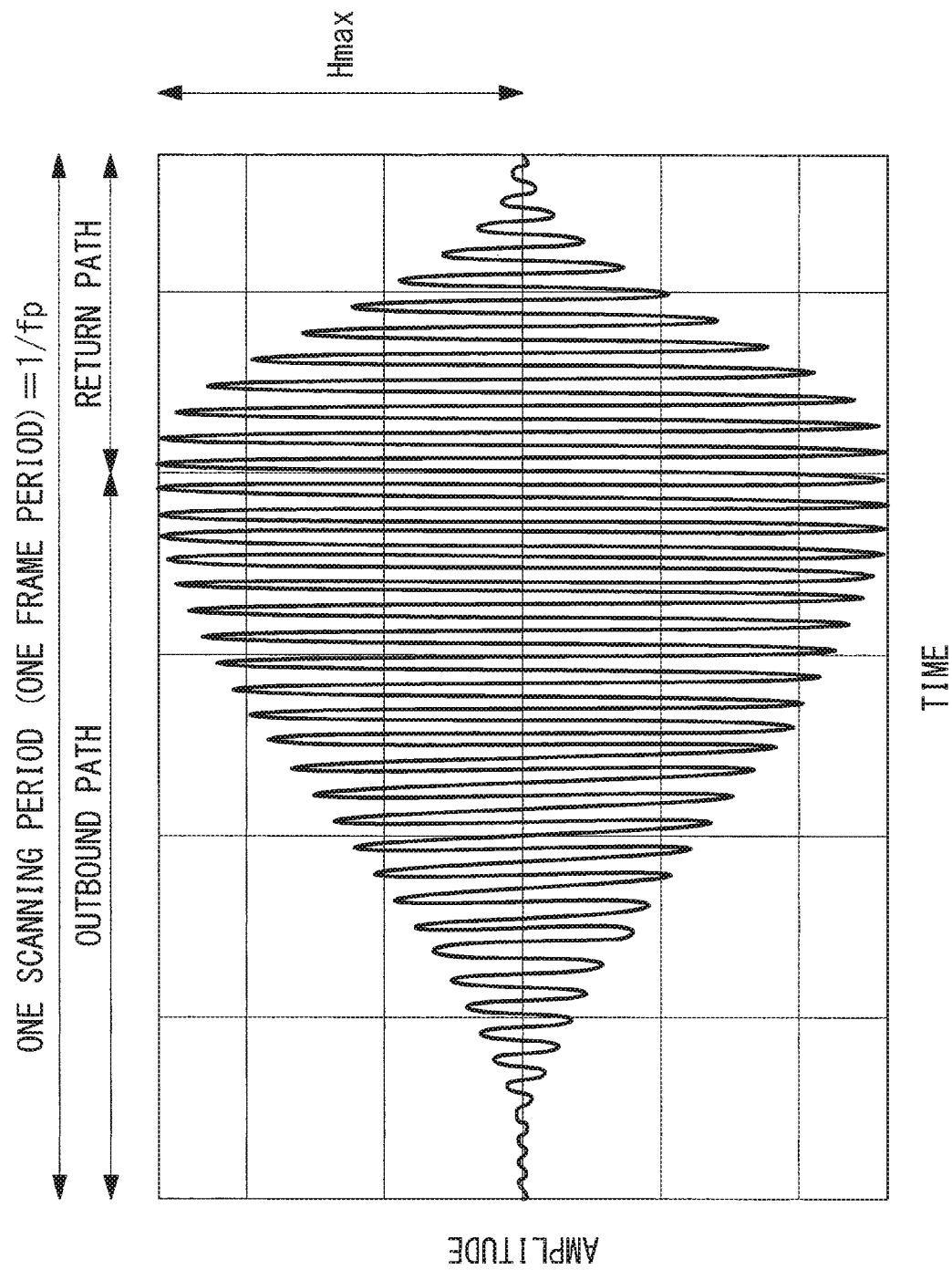

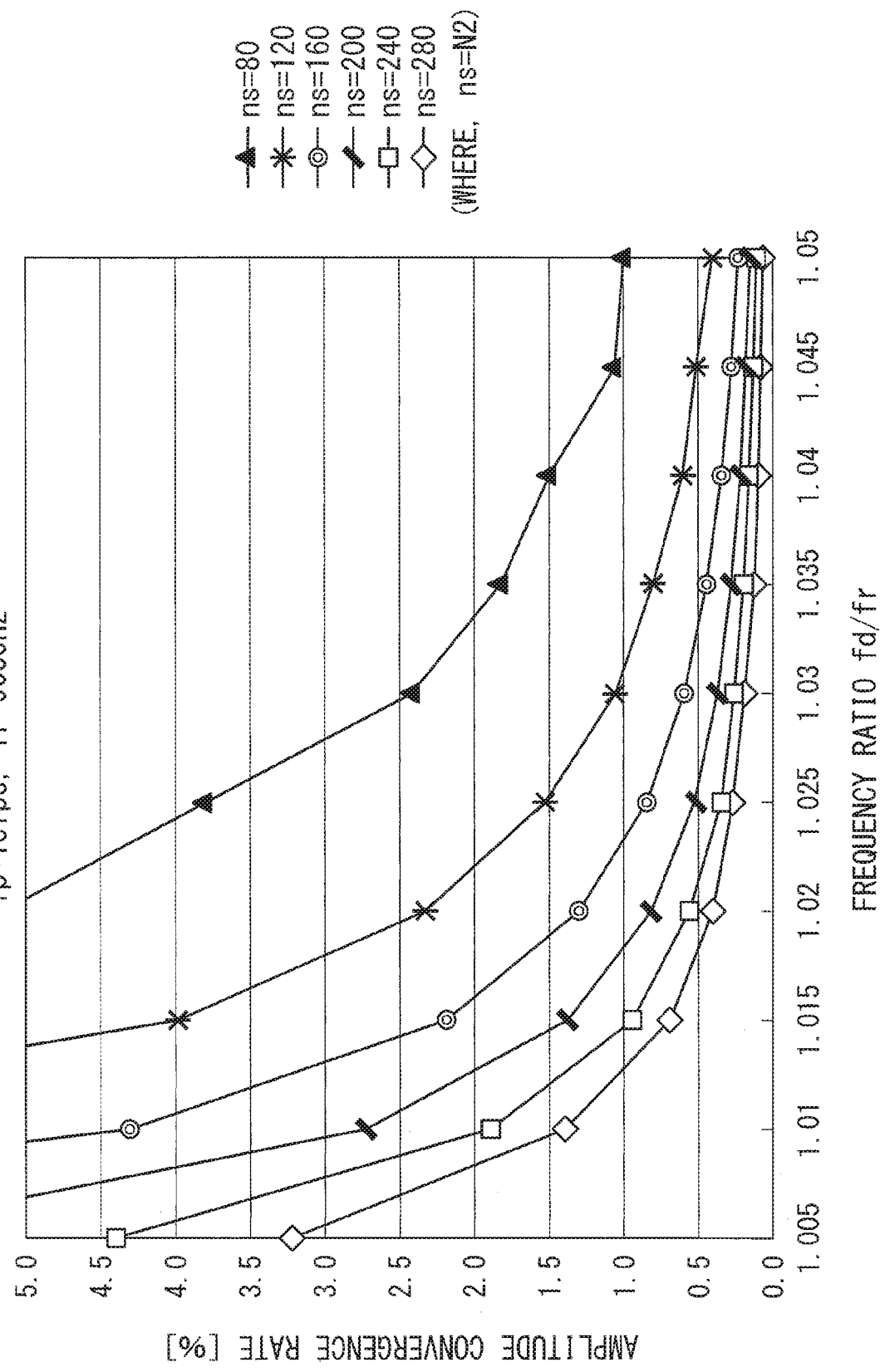

LIGHT-SCANNING APPARATUS AND LIGHT-SCANNING-APPARATUS CONTROL METHOD

CROSS-REFERENCE TO RELATED APPLICATIONS

This is a continuation of International Application PCT/JP2015/079864, with an international filing date of Oct. 22, 2015, which is hereby incorporated by reference herein in its entirety.

TECHNICAL FIELD

The present invention relates to a light-scanning apparatus and a light-scanning-apparatus control method.

BACKGROUND ART

In the related art, there is a known scanning endoscope apparatus employing a spiral scanning method (for example, see Patent Literature 1). In the spiral scanning method, by causing a distal end of an optical fiber to be oscillated along a spiral trajectory, illumination light emitted from the distal end of the optical fiber is scanned over an imaging subject along the spiral scanning trajectory.

CITATION LIST

Patent Literature

{PTL 1} Publication of Japanese Patent No. 5190267

SUMMARY OF INVENTION

An object of the present invention is to provide a light-scanning apparatus and a light-scanning-apparatus control method with which it is possible, in a spiral scanning method, to reliably cause oscillations of the distal end of an optical fiber to converge.

Solution to Problem

A first aspect of the present invention is a light-scanning apparatus including: an optical fiber that emits light from a distal end thereof; a signal-generating portion that generates a driving signal that has a frequency different from a resonant frequency of the optical fiber and that is for causing the distal end of the optical fiber to undergo spiral oscillations; and a driving portion that causes the distal end of the optical fiber to undergo spiral oscillations in accordance with the driving signal generated by the signal-generating portion, wherein the signal-generating portion generates the driving signal that includes, during one scanning period, a first period in which an amplitude gradually increases from substantially zero to a maximum value and a second period in which the amplitude gradually decreases from the maximum value to substantially zero, and that satisfies conditional expression (1) or conditional expression (2) below where fr is the resonant frequency of the optical fiber; fd is the frequency of the driving signal; and N2 is the number of oscillations of the driving signal in the second period.

{Eq. 1}

$$2 \geq \frac{1}{N2^2} \cdot \frac{12}{\left(\frac{fd}{fr} - 0.999\right)^2} \quad \left(\text{when } \frac{fd}{fr} > 1\right) \quad (1)$$

$$2 \geq \frac{1}{N2^2} \cdot \frac{12}{\left(1.001 - \frac{fd}{fr}\right)^2} \quad \left(\text{when } \frac{fd}{fr} < 1\right) \quad (2)$$

In the above-described first aspect, the signal-generating portion may generate the driving signal that satisfies conditional expression (3) below:

$$N2 \geq 60. \quad (3)$$

In the above-described first aspect, the signal-generating portion may generate the driving signal that satisfies conditional expression (4) or conditional expression (5) below:

$$fd/fr \geq 1.01; \quad (4)$$

$$fd/fr \leq 0.99. \quad (5)$$

A second aspect of the present invention is a light-scanning-apparatus control method in which light emitted from a distal end of an optical fiber is scanned on an imaging subject in a spiraling manner, the light-scanning-apparatus control method including: a signal-generating step of generating a driving signal that has a frequency different from a resonant frequency of the optical fiber and that is for causing the distal end of the optical fiber to undergo spiral oscillations; and a driving step of causing the distal end of the optical fiber to undergo spiral oscillations in accordance with the driving signal generated in the signal-generating step, wherein the signal-generating step generates the drive signal that includes, during one scanning period, a first period in which an amplitude gradually increases from substantially zero to a maximum value and a second period in which the amplitude gradually decreases from the maximum value to substantially zero, and that satisfies conditional expression (1) or conditional expression (2) below, where fr is the resonant frequency of the optical fiber; fd is the frequency of the driving signal; and N2 is the number of oscillations of the driving signal in the second period.

{Eq. 2}

$$2 \geq \frac{1}{N2^2} \cdot \frac{12}{\left(\frac{fd}{fr} - 0.999\right)^2} \quad \left(\text{when } \frac{fd}{fr} > 1\right) \quad (1)$$

$$2 \geq \frac{1}{N2^2} \cdot \frac{12}{\left(1.001 - \frac{fd}{fr}\right)^2} \quad \left(\text{when } \frac{fd}{fr} < 1\right) \quad (2)$$

BRIEF DESCRIPTION OF DRAWINGS

FIG. 3A is a longitudinal cross-sectional view taken along a longitudinal axis, showing the internal configuration of a distal-end portion of an inserted portion of an endoscope.

FIG. 4A is a diagram showing temporal changes, over one scanning period, in the amplitude of a distal end of an optical fiber undergoing spiral oscillations.

FIG. 5B is a graph showing further results of simulations for determining the relationship between the frequency ratio fd/fr and the amplitude convergence rate with respect to the number of oscillations N2 in the return path.

DESCRIPTION OF EMBODIMENT

A light-scanning apparatus 1 according to an embodiment of the present invention will be described below with reference to the drawings.

Figure 1:
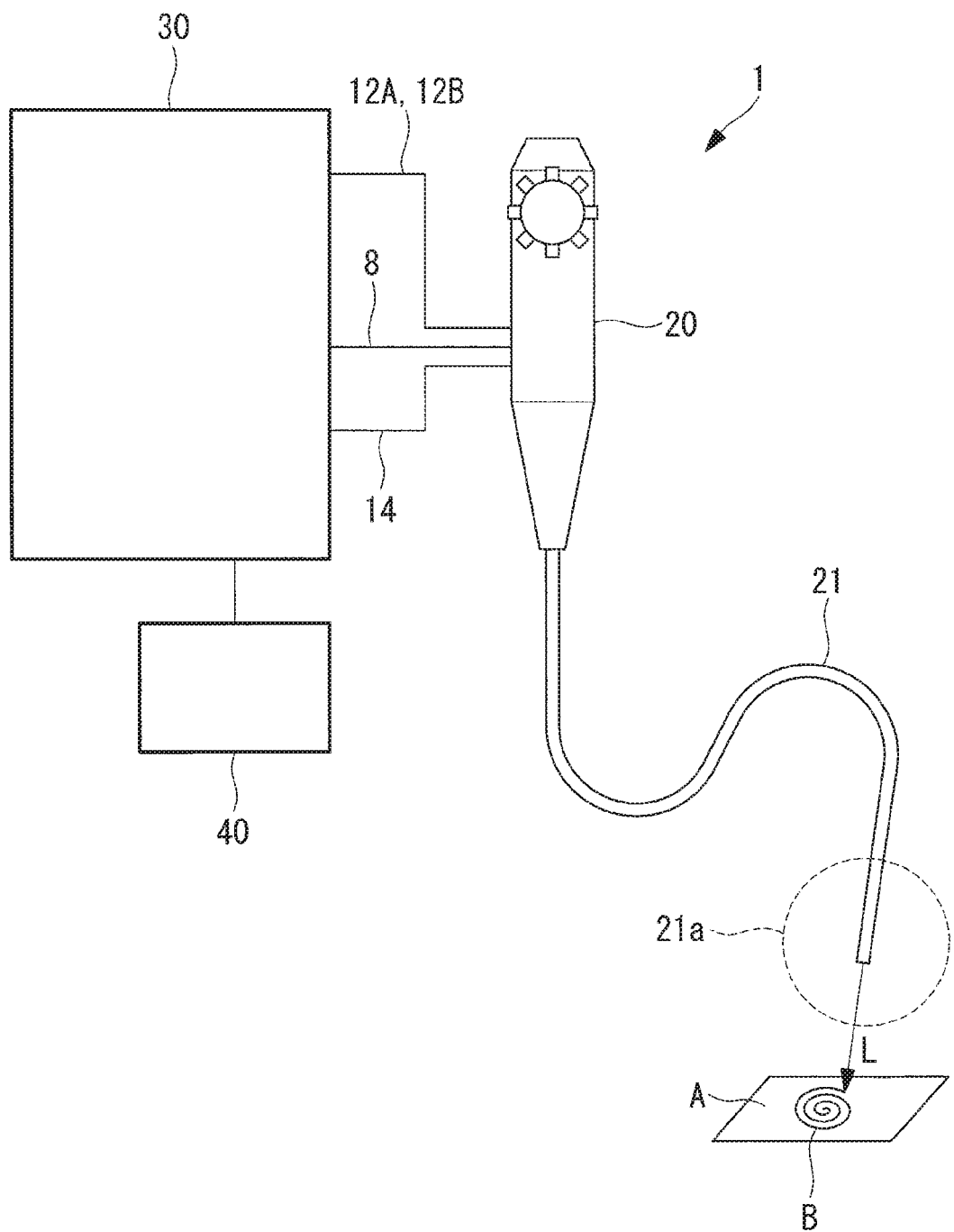
FIG. 1 is an overall configuration diagram of a light-scanning apparatus according to an embodiment of the present invention.

As shown in FIG. 1, the light-scanning apparatus 1 according to this embodiment is provided with an endoscope 20, a controller main unit 30, and a display 40, and is a light-scanning endoscope apparatus that scans laser light L emitted from a distal end of an inserted portion 21 of the endoscope 20 on an imaging subject A along a spiral scanning trajectory B, thus acquiring an image of the imaging subject A.

Figure 2:
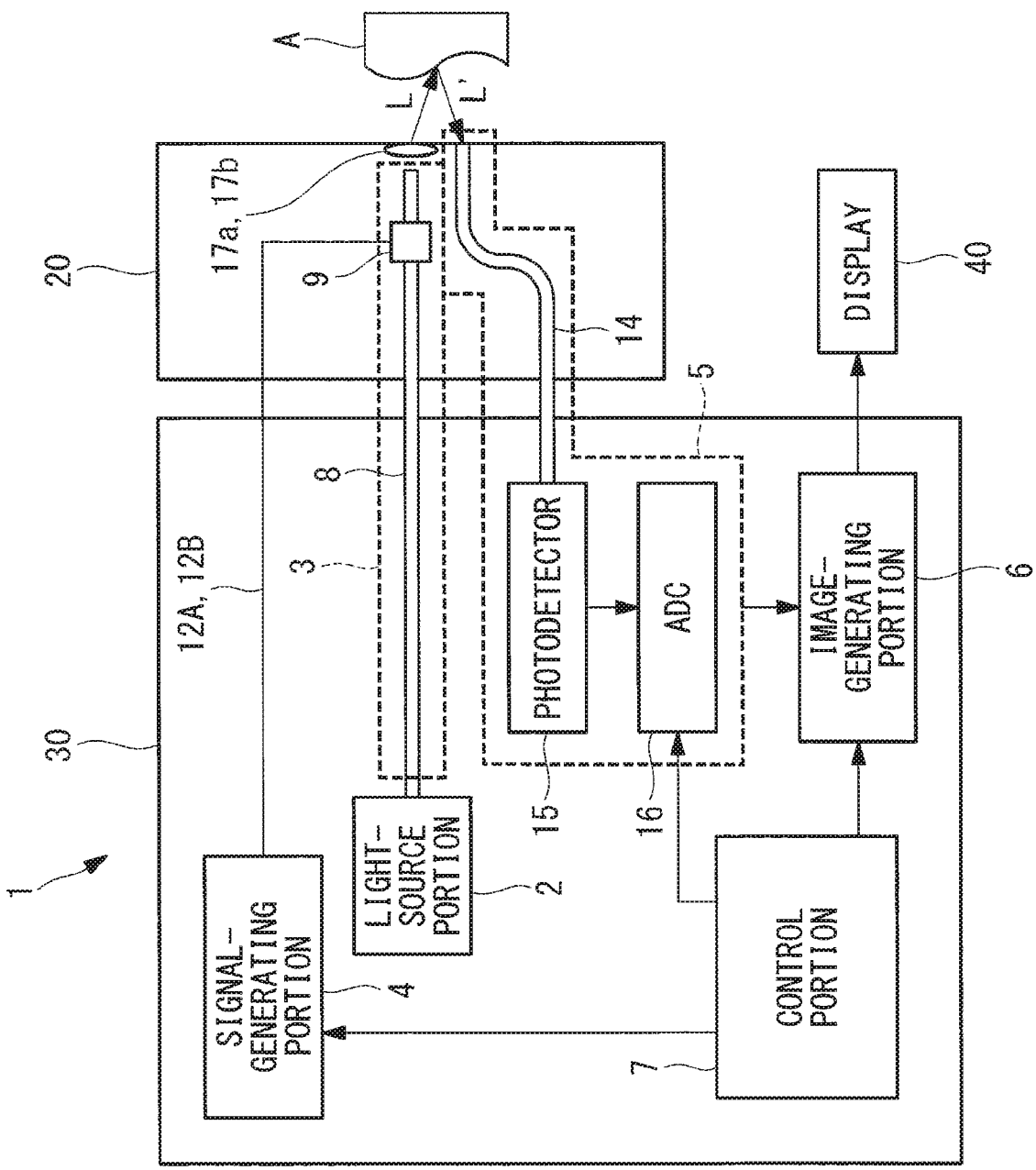
FIG. 2 is a detailed configuration diagram of the light-scanning apparatus in FIG. 1.

As shown in FIG. 2, the light-scanning apparatus 1 is provided with: a light-source portion 2; a light-scanning portion 3 that irradiates the imaging subject A while scanning the laser light L output from the light-source portion 2; a signal-generating portion 4 that generates driving signals for driving the light-scanning portion 3; a light-detecting portion 5 that detects observation light L' that is generated in the form of return light coming from the imaging subject A as a result of irradiation thereof with the laser light L; an image-generating portion 6 that generates an image of the imaging subject A on the basis of the observation light L' detected by the light-detecting portion 5; and a control portion 7 that controls the light-scanning portion 3, the signal-generating portion 4, the light-detecting portion 5, and the image-generating portion 6. The observation light L' is any one of reflected light, scattered light, and fluorescence coming from the imaging subject A.

The light-source portion 2 is provided with, for example, three laser light sources (not shown) that separately emit red, green, and blue laser light L, and sequentially outputs the red, green, and blue laser light L. As the laser light sources, for example, semiconductor-pumped solid-state lasers or laser diodes are employed.

The light-scanning portion 3 is provided with an irradiation optical fiber 8 that is disposed in the inserted portion 21 along the longitudinal direction and an actuator (driving portion) 9 that is provided at a distal-end portion 21a of the inserted portion 21 and that causes the irradiation optical fiber 8 to be oscillated.

A base end of the irradiation optical fiber 8 is connected to the light-source portion 2. The laser light L from the light-source portion 2 is incident on a base-end surface of the irradiation optical fiber 8, is guided in the interior of the irradiation optical fiber 8 from the base end to the distal end thereof, and is emitted into an area in front of the distal end of the inserted portion 21 from the distal-end surface of the irradiation optical fiber 8.

Figure 3B:
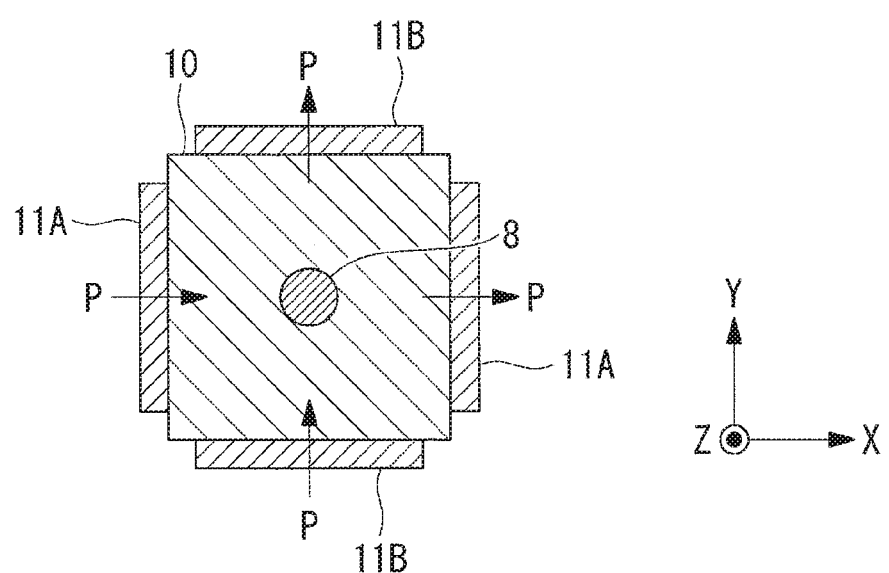
FIG. 3B is a lateral cross-sectional view taken along the line III-III in FIG. 3A.

As shown in FIGS. 3A and 3B, the actuator 9 is provided with a rectangular tube-shaped elastic portion 10 and four piezoelectric elements 11A and 11B that are secured to outer circumferential surfaces of the elastic portion 10. Reference signs 17a and 17b indicate scanning lenses for focusing the laser light L.

The irradiation optical fiber 8 passes through the interior of the elastic portion 10, and the elastic portion 10 is secured to an outer circumferential surface of the irradiation optical fiber 8 at a position that is separated from a distal end 8a toward the base end of the irradiation optical fiber 8. A portion of the elastic portion 10 that is closer to the base end than the piezoelectric elements 11A and 11B are is secured to an outer cylinder of the inserted portion 21 via a securing portion 13. By doing so, distal-end portions of the elastic portion 10 and the irradiation optical fiber 8 are supported in a cantilever-like manner, thus being oscillatable.

The piezoelectric elements 11A and 11B are plate-like and polarized in the thickness directions. In FIG. 3B, arrows P indicate the polarization directions of the piezoelectric elements 11A and 11B. As shown in FIG. 3B, the piezoelectric elements 11A and 11B are secured, individually, to the individual four outside surfaces of the elastic portion 10 so that the polarization directions of the two piezoelectric elements 11A or 11B facing each other in the radial directions of the irradiation optical fiber 8 are oriented in the same directions. Phase-A electrical cables 12A are connected to the two X-scanning piezoelectric elements 11A facing each other in the X-direction, and phase-B electrical cables 12B are connected to the two Y-scanning piezoelectric elements 11B facing each other in the Y-direction. The X- and Y-directions are directions that are radial directions of the irradiation optical fiber 8 and that are orthogonal to each other.

The signal-generating portion 4 generates, as driving signals, two AC voltages of phase A and phase B that have frequencies and amplitudes specified by control signals received from the control portion 7. The phase-A driving signals are supplied to the two X-scanning piezoelectric elements 11A via the electrical cables 12A, and the phase-B driving signals are supplied to the two Y-scanning piezoelectric elements 11B via the electrical cables 12B.

When the phase-A driving signals are applied to the X-scanning piezoelectric elements 11A, the piezoelectric elements 11A undergo stretching vibrations in the longitudinal direction (Z-direction) of the irradiation optical fiber 8. At this time, one of the two piezoelectric elements 11A contracts in the Z-direction and the other stretches in the Z-direction, thus exciting bending vibrations in the elastic portion 10 in the X-direction with a node positioned at the position of the securing portion 13. The bending vibrations of the elastic portion 10 are transmitted to the irradiation optical fiber 8. By doing so, the distal-end portion of the irradiation optical fiber 8 is made to undergo bending vibrations in the X-direction, which causes the distal end 8a of the irradiation optical fiber 8 to be oscillated in the X-direction, and thus, the laser light L emitted from the distal end 8a is scanned in the X-direction.

When the phase-B driving signals are applied to the Y-scanning piezoelectric elements 11B, the piezoelectric elements 11B undergo stretching vibrations in the longitudinal direction (Z-direction) of the irradiation optical fiber 8. At this time, one of the two piezoelectric elements 11B contracts in the Z-direction, and the other stretches in the Z-direction, thus exciting bending vibrations in the elastic portion 10 in the Y-direction with a node positioned at the position of the securing portion 13. The bending vibrations of the elastic portion 10 are transmitted to the irradiation optical fiber 8. By doing so, the distal-end portion of the irradiation optical fiber 8 is made to undergo bending vibrations in the Y-direction, which causes the distal end 8a of the irradiation optical fiber 8 to be oscillated in the Y-direction, and thus, the laser light L emitted from the distal end 8a is scanned in the Y-direction.

Here, the signal-generating portion 4 generates, in accordance with the control signals, the phase-A driving signals and the phase-B driving signals that include, during one scanning period, an outbound path (first period) in which the amplitude gradually increases from substantially zero to a maximum value and a return path (second period) in which the amplitude gradually decreases from the maximum value to substantially zero, and that have phases that are shifted from each other by substantially π/4. By doing so, as shown in FIG. 4A, the actuator 9 causes the distal end 8a of the irradiation optical fiber 8 to undergo spiral oscillations along a spiral trajectory.

Figure 4B:
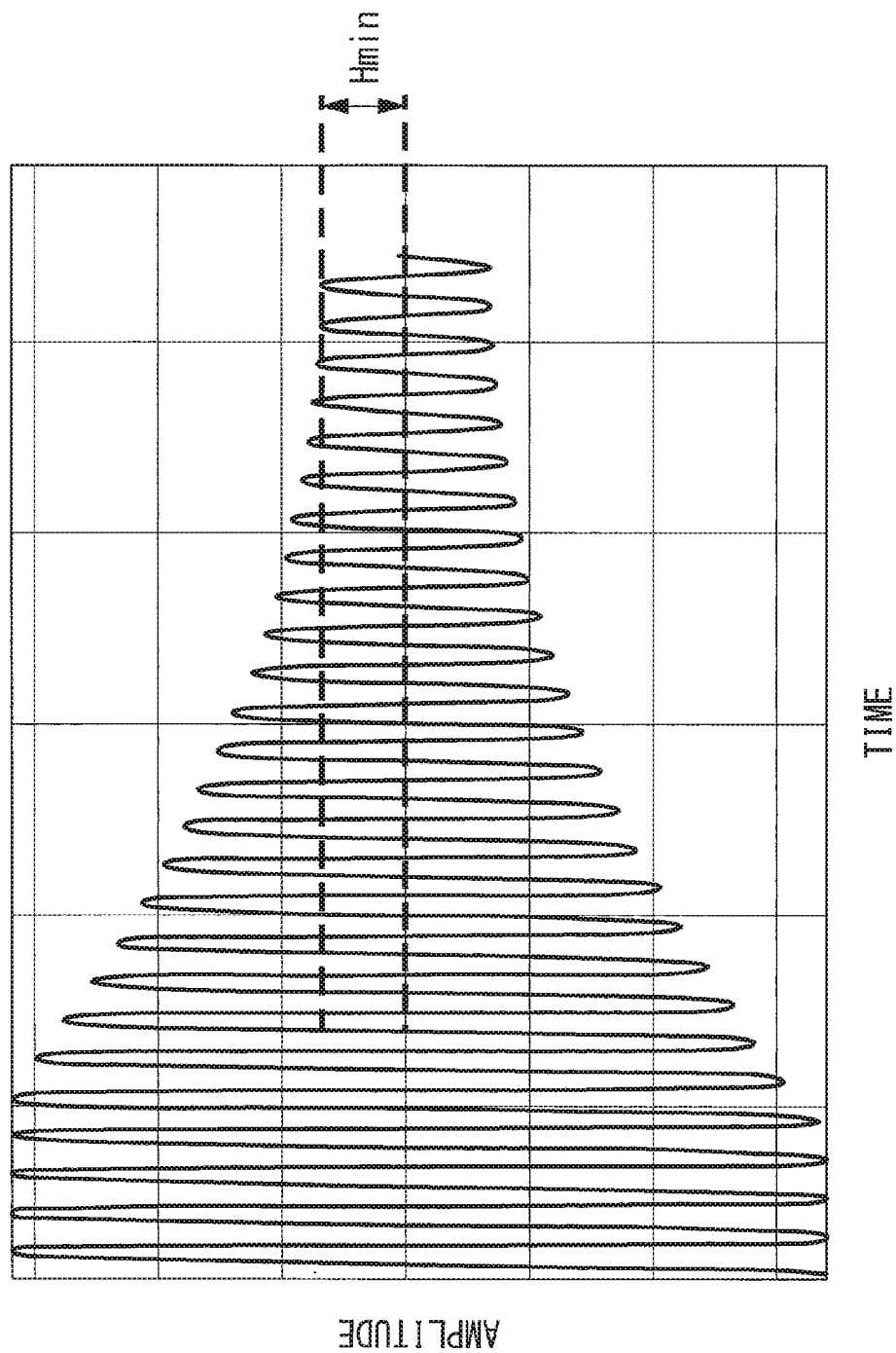
FIG. 4B is a diagram in which a final portion of a return path in FIG. 4A is enlarged.

FIGS. 4A and 4B show changes over time of the amplitude of the distal end 8a of the optical fiber 8 in the X-direction or the Y-direction. As shown in FIGS. 4A and 4B, the amplitude of the distal end 8a gradually increases from a minimum value Hmin to a maximum value Hmax in the outbound path, and decreases from the maximum value Hmax to the minimum value Hmin in the return path. The maximum value Hmax of the amplitude corresponds to the radius of an image-capturing area. The changes over time of the amplitude shown in FIG. 4A correspond to a scanning trajectory extracted for one scanning period (one frame period). In the subsequent frame and thereafter, changes over time having nearly the same amplitude as shown in this graph are repeated.

The light-detecting portion 5 is provided with: a light-receiving optical fiber 14 that receives, at a distal end thereof, the observation light L' (for example, reflected light of the laser light L or fluorescence excited by the laser light L) generated at the imaging subject A; a photodetector 15, such as a photomultiplier tube, that detects the observation light L' received by the light-receiving optical fiber 14; and an A/D converter 16 that performs analog-to-digital (AD) conversion of electrical signals output from the photodetector 15.

The distal end of the light-receiving optical fiber 14 is disposed at the distal-end surface of the inserted portion 21, and the base end of the light-receiving optical fiber 14 is connected to the photodetector 15.

The photodetector 15 generates electrical signals in accordance with the intensity of the observation light L' by photoelectrically converting the observation light L' incident on the light-receiving optical fiber 14, and outputs the generated electrical signals to the A/D converter 16.

The A/D converter 16 obtains digital values indicating the intensity of the observation light L' by performing AD conversion by sampling the electrical signals input from the photodetector 15 in synchronization with sampling signals received from the control portion 7. The A/D converter 16 transmits the obtained digital values to the image-generating portion 6.

As described above, the control portion 7 generates the control signals for causing the signal-generating portion 4 to generate the driving signals including those for the outbound path and the return path, and transmits the control signals to the signal-generating portion 4.

Furthermore, the control portion 7 sets a driving-signal frequency (drive frequency) fd and numbers of oscillations N, N1, and N2, and generates the control signals for causing the signal-generating portion 4 to generate driving signals having the set drive frequency fd and numbers of oscillations N, N1, and N2.

The number of oscillations N is the total number of oscillations of the driving signals during one scanning period (one frame period), the number of oscillations N1 is the number of oscillations of the driving signals in the outbound path, and the number of oscillations N2 is the number of oscillations of the driving signals in the return path. The number of oscillations of the driving signals corresponds to the spiral scanning trajectory or the number of laps in the oscillation trajectory (the number of circles when the scanning trajectory is considered to be a collection of concentric circles). Therefore, in the following, the numbers of oscillations N, N1, and N2 are also referred to as the numbers of laps N, N1, and N2.

Here, the control portion 7 sets the drive frequency fd and the number of laps N2 in the return path so as to satisfy conditional expression (1), where the drive frequency fd is greater than a resonant frequency fr of the distal-end portion of the optical fiber 8. Furthermore, the drive frequency fd and the total number of laps N of the driving signals in one frame period satisfy N≤fd/fp, where fp is the frame rate of the image.

{Eq. 3}

$$2 \geq \frac{1}{N2^2} \cdot \frac{12}{\left(\frac{fd}{fr} - 0.999\right)^2} \left( \text{when } \frac{fd}{fr} > 1 \right) \quad (1)$$

For example, in the case in which the frame rate fp is 30 Hz and the drive frequency fd is 9000 Hz, the total number of laps N during one scanning period is 9000/30=300. Between the number of laps N1 in the outbound path and the number of laps N2 in the return path, N1+N2≤N holds. For example, as shown in FIG. 4A, modulated waveforms in the outbound path and the return path take a sine wave shape, and, when N1=200 and N2=100, the frequency of the modulated waves in the outbound path is fd/2/N1=22.5 Hz, and the frequency of the modulated waves in the return path is fd/2/N2=45 Hz. In this case, because N1+N2=N, the period in which the amplitude of the fiber reaches zero is the only period in which the driving signals reach zero. In the case in which N1+N2<N, a period in which the driving signals are continuously zero is provided in a period in one of the outbound path and the return path.

In addition, the control portion 7 computes, on the basis of the control signals, positions on the imaging subject A that are irradiated with the laser light L by means of the light-scanning portion 3 when the A/D converter 16 performs sampling of the electrical signals in accordance with the sampling signals, and transmits information about the calculated irradiation positions to the image-generating portion 6.

The image-generating portion 6 generates a two-dimensional image of the imaging subject A by associating the digital values received from the A/D converter 16 with the information about the irradiation positions of the observation light L' received from the control portion 7. The image-generating portion 6 transmits the generated image to the display 40 to be displayed thereon.

Next, the operation of the thus-configured light-scanning apparatus 1 according to this embodiment will be described.

In order to observe the interior of the body of a patient by using the light-scanning apparatus 1 according to this embodiment, the inserted portion 21 is inserted into the body, and the distal end of the inserted portion 21 is made to face the biological tissue that serves as the imaging subject A. By doing so, the laser light L irradiates the imaging subject A from the distal end 8a of the irradiation optical fiber 8. At this time, by causing the distal end 8a of the irradiation optical fiber 8 to undergo spiral oscillations by means of the actuator 9, the laser light L is scanned over the imaging subject A in a spiraling manner.

The observation light L' generated at the irradiation positions of the laser light L is received at the distal end of the light-receiving optical fiber 14, the intensity of the observation light L' is detected by the photodetector 15, and the digital values of the intensity of the observation light L' are obtained by the A/D converter 16. The obtained digital values are transmitted to the image-generating portion 6. In the image-generating portion 6, the digital values received from the A/D converter 16 are stored in association with the irradiation positions of the laser light L received from the control portion 7, and thus an image is generated. The generated image is displayed on the display 40.

Here, as described above, the control portion 7 causes the signal-generating portion 4 to generate the driving signals having the frequency ratio fd/fr (where, fd>fr) and the number of laps N2 that satisfy conditional expression (1) (signal-generating step), and the actuator 9 causes the distal end 8a of the irradiation optical fiber 8 to undergo spiral oscillations in accordance with the driving signals (driving step).

In the return path, the oscillations of the distal end 8a of the optical fiber 8 are attenuated when the amplitude of the driving signals gradually decreases, and thus, the laser light L is scanned in a spiraling manner radially from the outside of the scanning trajectory toward the center thereof. At this time, in the case in which the attenuation of the oscillations of the optical fiber 8 is insufficient, the laser light L is not radiated in the center region of the scanning trajectory in the next frame, and thus, pixels that do not have information about the intensity of the observation light L' (hereinafter, referred to as defective pixels) occur in the center region of the image. Here, the above-described defective pixels may occur when an image is generated during either one of the scanning period on the outbound-path side in FIG. 4A and the scanning period on the return-path side in FIG. 4A.

The ease of attenuating the oscillations of the distal end 8a of the irradiation optical fiber 8 depends on the oscillation characteristics (for example, the resonant frequency and the attenuation coefficient) of the irradiation optical fiber 8 and driving-signal conditions, and attenuation thereof becomes more difficult to achieve when the drive frequency fd approaches the resonant frequency fr of the irradiation optical fiber 8. The following amplitude convergence rate is defined as an indicator for indicating an attenuation characteristic of the oscillations of the distal end 8a of the irradiation optical fiber 8.

Amplitude convergence rate=[Minimum value $H$min of amplitude of distal end of optical fiber]/ [Maximum value $H$max of amplitude of distal end of optical fiber]×100[%]

Here, in FIG. 4B, although the minimum value Hmin is defined on the return-path side, because amplitude changes in FIG. 4A are continuously repeated, the result is the same even if the minimum value Hmin is defined on the outbound-path side.

In order for the light-scanning endoscope apparatus to obtain a greater resolution as compared to an imaging light guide that has a similarly small diameter and that employs bundled fibers, it is desirable that the image acquired by the light-scanning endoscope apparatus have a pixel number that is at least equal to or greater than 100×100 pixels. Assuming that the amplitude convergence rate is 2% in the 100×100-pixel image, the number of defective pixels in the center region thereof is 100×0.02=2 pixels. If the number of defective pixels is equal to or less than 2 pixels, it is possible to interpolate the pixel values of the defective pixels by means of image processing; however, in the case in which the number of the defective pixels is equal to or greater than 3 pixels, it is difficult to interpolate the pixel values of the defective pixels by means of image processing. Therefore, it is important to suppress the amplitude convergence rate to be equal to or less than 2% in the light-scanning endoscope apparatus.

Figure 5A:
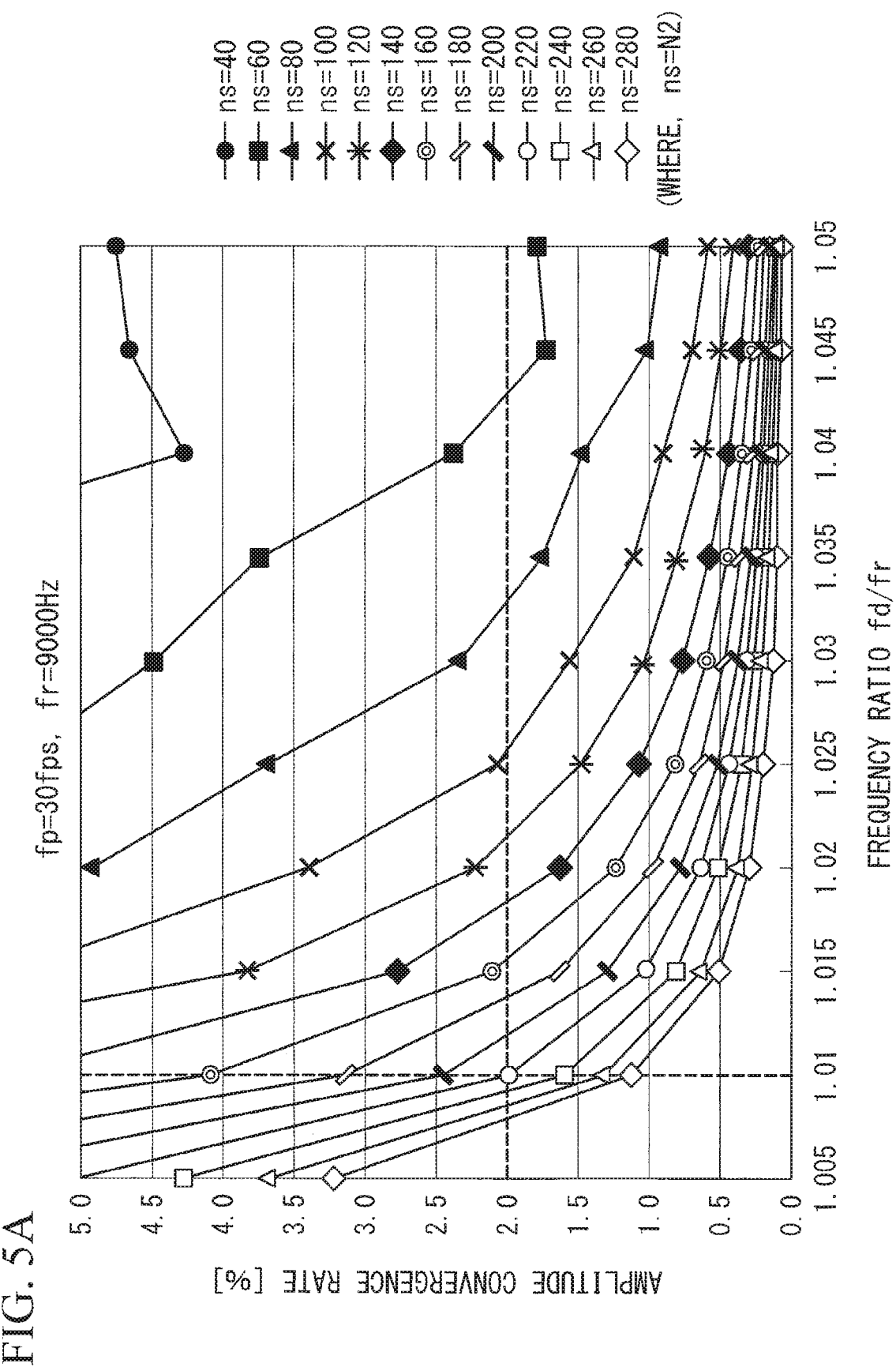
FIG. 5A is a graph showing results of simulations for determining the relationship between the frequency ratio fd/fr and the amplitude convergence rate with respect to the number of oscillations N2 in the return path.
Figure 5C:
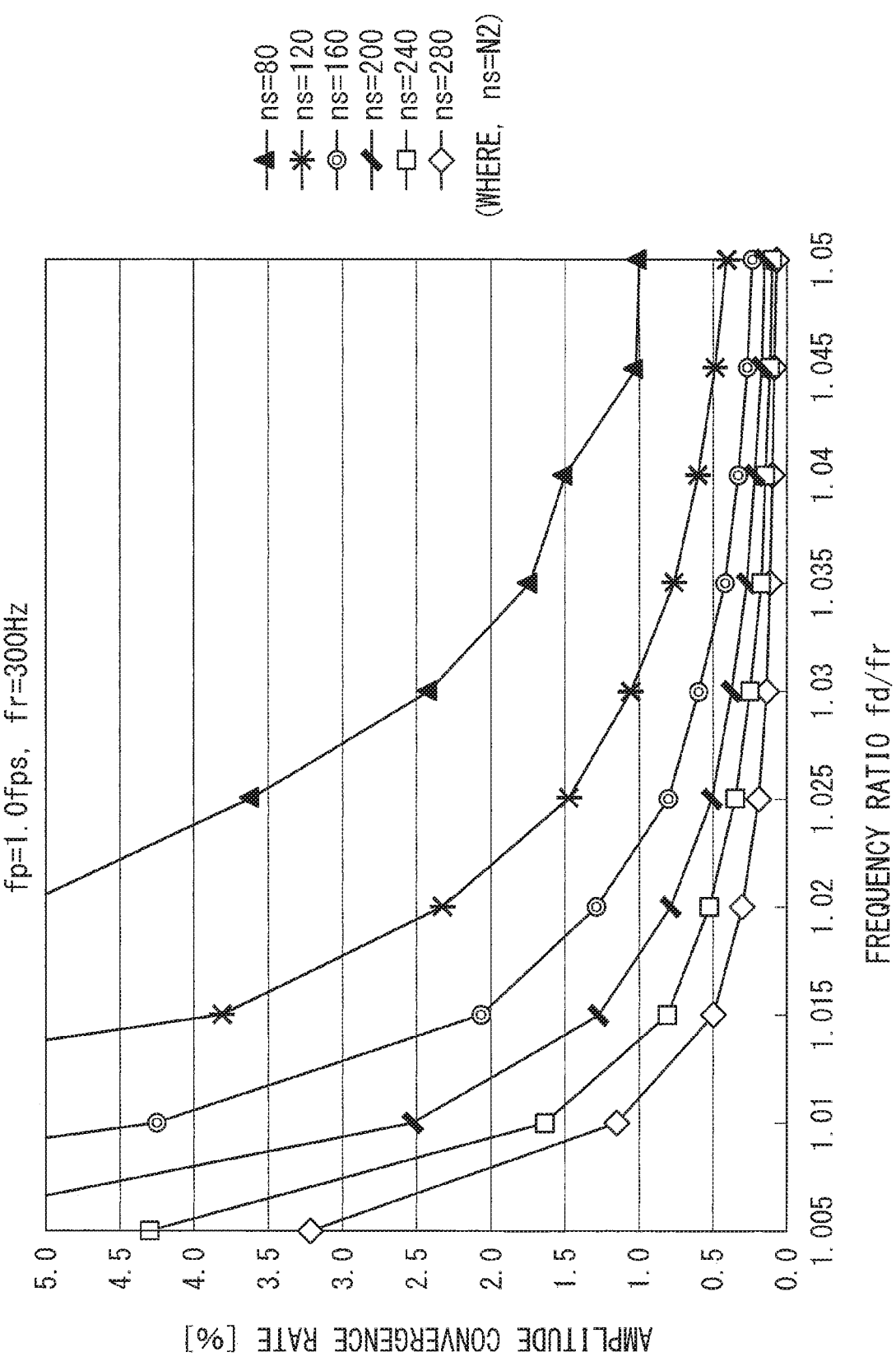
FIG. 5C is a graph showing further results of simulations for determining the relationship between the frequency ratio fd/fr and the amplitude convergence rate with respect to the number of oscillations N2 in the return path.

FIG. 5A shows the results of simulating the amplitude convergence rate by changing the number of laps N2 and the drive frequency fd in the return path. In the simulations, the frame rate fp was set to 30 fps and the resonant frequency fr was set to 9000 Hz. Furthermore, the simulation results when the frame rate fp was set to 15 fps and the resonant frequency fr was set to 9000 Hz are shown in FIG. 5B, and the simulation results when the frame rate fp was set to 1 fps and the resonant frequency fr was set to 300 Hz are shown in FIG. 5C. From the simulation results shown in FIGS. 5A to 5C, it is clear that the amplitude convergence rate strongly depends on the number of laps N2 in the return path and the ratio (frequency ratio) fd/fr of the drive frequency fd to the resonant frequency fr.

Figure 6:
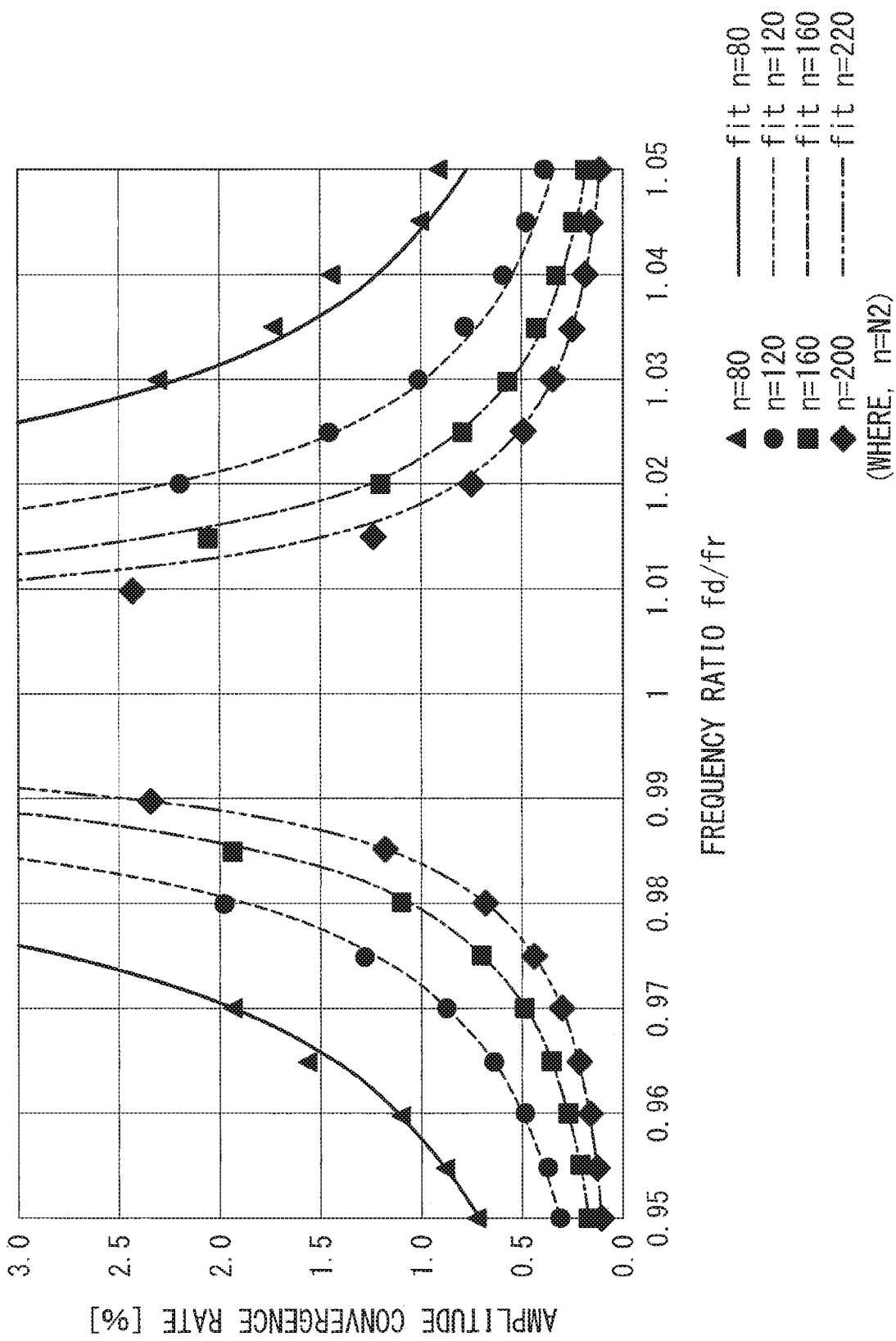
FIG. 6 is a graph showing further results of simulations for determining the relationship between the frequency ratio fd/fr and the amplitude convergence rate with respect to the number of oscillations N2 in the return path.

In FIG. 6, curves are fitted to the data points at N2=80, 120, 160, and 200 in FIG. 5A. The amplitude convergence rate is inversely proportional to the square of the number of laps N2 in the return path, and is inversely proportional to the square of the frequency ratio fd/fr. Therefore, conditional expression (1) is derived as the condition for the frequency ratio fd/fr and the number of laps N2 to keep the amplitude convergence rate at 2% or less.

As has been described above, with this embodiment, by causing the distal end 8a of the optical fiber 8 to undergo spiral oscillations by means of the driving signals that satisfy conditional expression (1), it is possible, at the end of the return path, to reliably cause the amplitude of the distal end of the optical fiber 8 to converge so as to reach a value that is equal to or less than 2% of the maximum value Hmax. By doing so, there is an advantage in that it is possible to acquire an image without a defect by suppressing the number of defective pixels to 2 pixels or less. Furthermore, by bringing the drive frequency fd close to the resonant frequency fr within a range in which the conditional expression (1) is satisfied, it is possible to increase the amplitude of the distal end 8a of the irradiation optical fiber 8 while suppressing, as much as possible, the voltages to be applied to the piezoelectric elements 11A and 11B. In this specification, causing the optical fiber to oscillate at a drive frequency that is neither resonant drive nor non-resonant drive is referred to as quasi-resonance.

In this embodiment, it is preferable that the driving signals satisfy conditional expression (3).

$$N2 \geq 60 \tag{3}$$

As shown in FIG. 5A, in the case in which the number of laps N2 in the return path is equal to or greater than 60, the amplitude convergence rate is equal to or less than 2% within the practical range of the drive frequency fd with which it is possible to achieve quasi-resonance in the optical fiber 8. On the other hand, in the case in which the number of laps N2 in the return path is less than 60, because it is necessary to make the drive frequency fd greatly differ from the resonant frequency fr in order to suppress the amplitude convergence rate to be equal to or less than 2%, it is not possible to achieve quasi-resonance in the optical fiber 8, and thus, the amplitude of the distal end 8a is decreased.

Regardless of on which one of the outbound-path side and the return-path side the image is generated, the amplitude convergence rate depends on the number of laps N2 in the return path instead of the number of laps N1 in the outbound path, as indicated by conditional expression (3). The reason for this will be described next.

Figure 8:
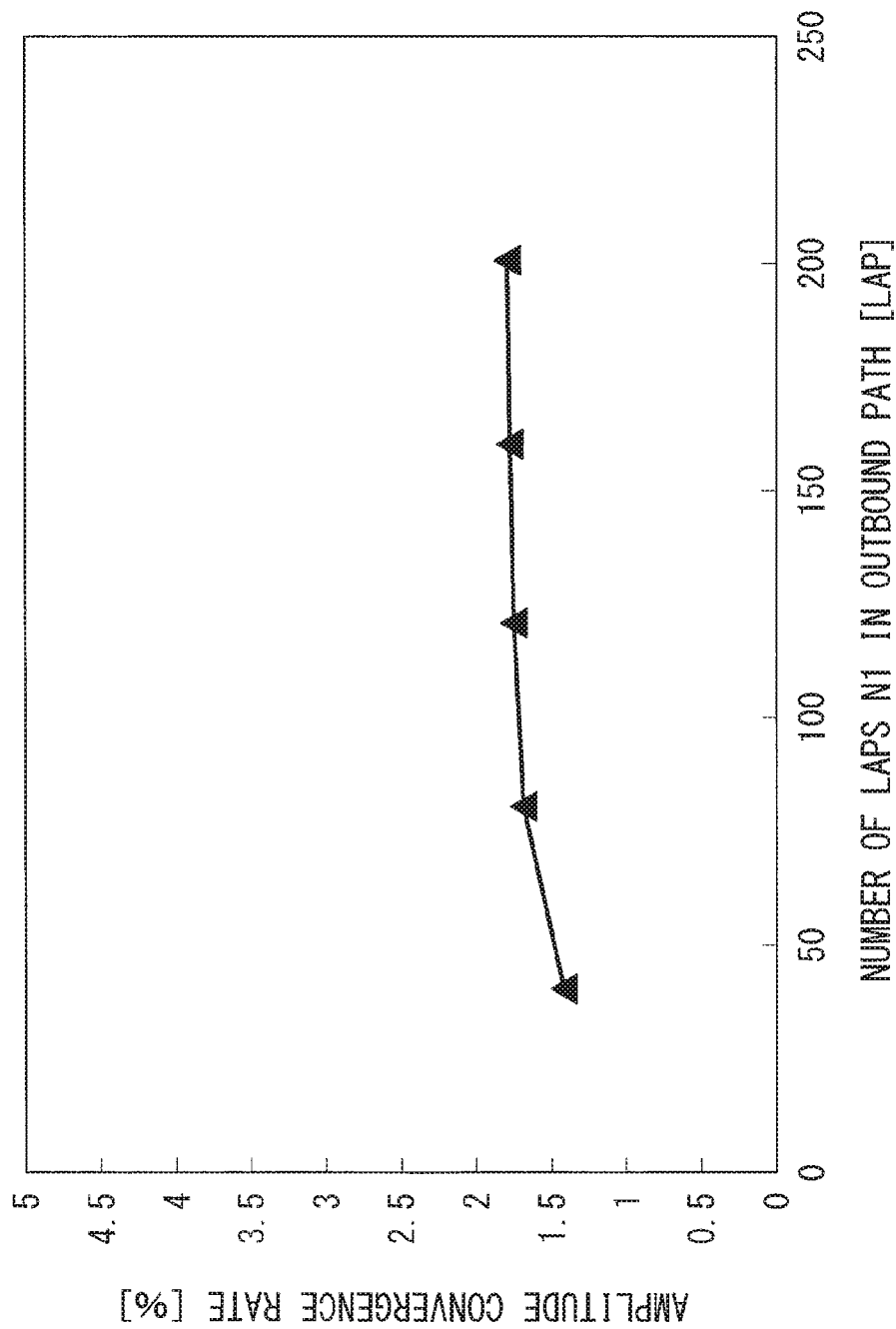
FIG. 8 is a graph showing the relationship between the number of laps the optical fiber has traveled in the outbound path and the amplitude convergence rate.

FIG. 8 shows changes in the amplitude convergence rate when the number of laps N2 in the return path is fixed to 60 laps and the number of laps N1 in the outbound path is changed. Here, the resonant frequency fr is set to be 9000 Hz and the frequency ratio fd/fr is set to be 1.05. As is clear from FIG. 8, the amplitude convergence rate does not greatly depend on the number of laps N1 in the outbound path. This fact can be explained as follows.

When scanning the outermost periphery of the scanning trajectory, the kinetic energy of the optical fiber 8 reaches a maximum. On the other hand, when scanning the vicinity of the center of the scanning trajectory, the kinetic energy of the optical fiber 8 is decreased. Therefore, in order to cause the oscillations of the distal end 8a of the optical fiber 8 to converge on the return-path side, it is necessary to gradually decrease the kinetic energy. Because the amount of time spent to decrease the kinetic energy is decreased when the number of laps N2 in the return path is decreased, the next frame starts in a state in which the kinetic energy has not been sufficiently decreased. As a result, the convergence of the amplitude is deteriorated. Here, a case in which the optical fiber 8 undergoes, when scanning is performed in a spiraling manner, a motion at a constant angular velocity without depending on the number of laps is assumed.

In addition, in this embodiment, it is preferable that the driving signals satisfy conditional expression (4).

$$fd/fr \geq 1.01 \tag{4}$$

The number of laps N2 required to suppress the amplitude convergence rate to be equal to or less than 2% is increased when the drive frequency fd is closer to the resonant frequency fr. In the case in which fd/fr is equal to or greater than 1.01, it is possible to achieve an amplitude convergence rate that is equal to or less than 2% in a practical range of the number of laps N2. On the other hand, when fd/fr is less than 1.01, the amount of time required for the return path is increased, thus resulting in a decrease in the frame rate.

In addition, in this embodiment, although the drive frequency fd is assumed to be greater than the resonant frequency fr, alternatively, the drive frequency fd may be less than the resonant frequency fr. In this case, the control portion 7 generates control signals for causing the signal-generating portion 4 to generate driving signals that satisfy conditional expression (2) instead of conditional expression (1).

{Eq. 4}

$$2 \geq \frac{1}{N2^2} \cdot \frac{12}{\left(1.001 - \frac{fd}{fr}\right)^2} \left( \text{when } \frac{fd}{fr} < 1 \right) \tag{2}$$

As shown in FIG. 6, curves fitted to the amplitude convergence rates are symmetrically centered on the frequency ratio=1. Therefore, in the case in which the frequency ratio fd/fr is less than 1, it is possible to achieve an amplitude convergence rate that is equal to or less than 2% by satisfying conditional expression (2).

In this case also, it is preferable that conditional expression (3) be satisfied.

Furthermore, it is preferable that conditional expression (5) be satisfied instead of conditional expression (4).

$$fd/fr \leq 0.99 \tag{5}$$

Figure 7:
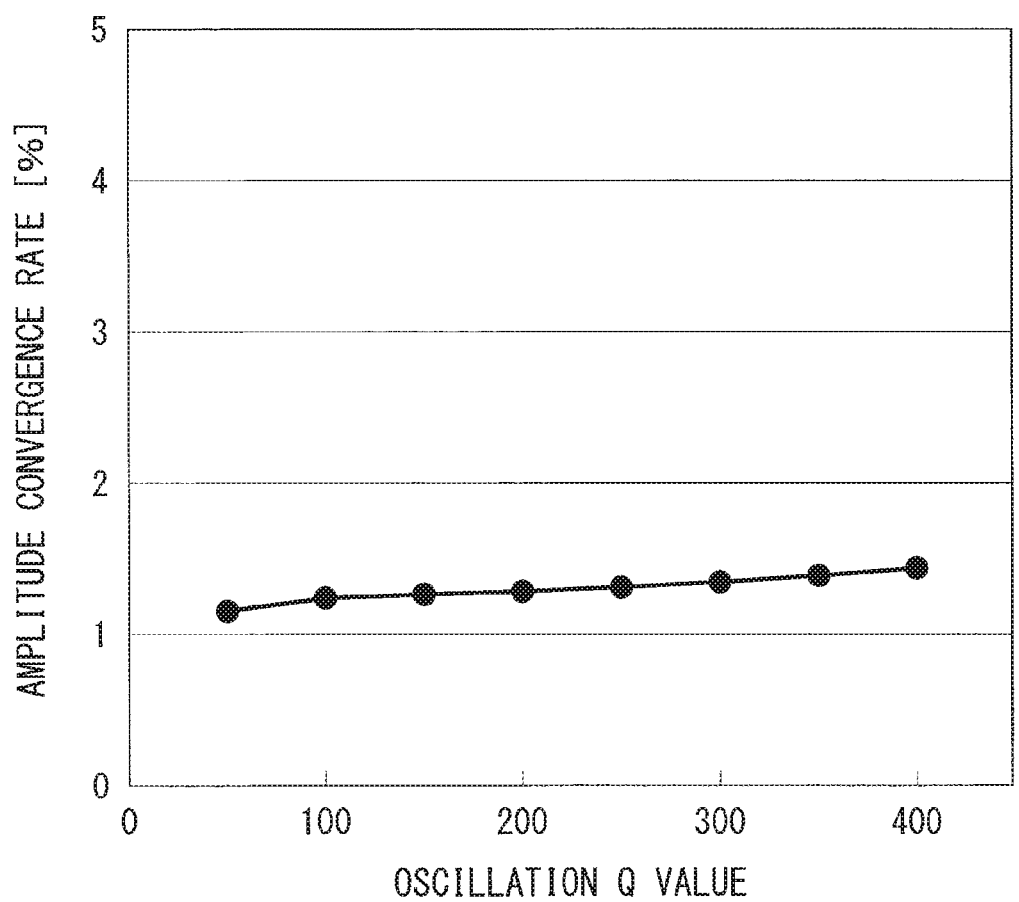
FIG. 7 is a graph showing the relationship between the Q value of the optical fiber and the amplitude convergence rate.

In addition, in this embodiment, the irradiation optical fiber 8 having a Q value that is equal to or less than 400 is employed. The Q value is expressed as $Q=1/(2\zeta)$ by using an attenuation coefficient $\zeta$ of the optical fiber. As shown in FIG. 7, although the amplitude convergence rate also increases with an increase in the Q value, the rate of increase of the amplitude convergence rate is low. FIG. 7 shows the relationship between the Q value and the amplitude convergence rate when fd/fr=1.03 and the number of laps N2=100 for the return path. Therefore, in a range in which the Q value is equal to or less than 400, the amplitude convergence rate does not substantially depend on the Q value.

As has been described above, it was found that it is possible to suppress the amplitude convergence rate to be equal to or less than a desired value by satisfying at least conditional expression (1) or (2). Furthermore, by additionally satisfying conditional expressions (3) to (5), it is possible to achieve both quasi-resonance and a low amplitude convergence rate. By employing these conditions, it is not necessary to perform a comprehensive search for conditions with which scanning in a spiraling manner is driven so as to enhance the convergence in the optical fiber 8, and it is possible to uniquely set the driving conditions.

As a result, the following aspect is read from the above described embodiment of the present invention.

A first aspect of the present invention is a light-scanning apparatus including: an optical fiber that emits light from a distal end thereof; a signal-generating portion that generates a driving signal that has a frequency different from a resonant frequency of the optical fiber and that is for causing the distal end of the optical fiber to undergo spiral oscillations; and a driving portion that causes the distal end of the optical fiber to undergo spiral oscillations in accordance with the driving signal generated by the signal-generating portion, wherein the signal-generating portion generates the driving signal that includes, during one scanning period, a first period in which an amplitude gradually increases from substantially zero to a maximum value and a second period in which the amplitude gradually decreases from the maximum value to substantially zero, and that satisfies conditional expression (1) or conditional expression (2) below where fr is the resonant frequency of the optical fiber; fd is the frequency of the driving signal; and N2 is the number of oscillations of the driving signal in the second period.

{Eq. 1}

$$2 \geq \frac{1}{N2^2} \cdot \frac{12}{\left(\frac{fd}{fr} - 0.999\right)^2} \left(\text{when } \frac{fd}{fr} > 1\right) \quad (1)$$

$$2 \geq \frac{1}{N2^2} \cdot \frac{12}{\left(1.001 - \frac{fd}{fr}\right)^2} \left(\text{when } \frac{fd}{fr} < 1\right) \quad (2)$$

With the first aspect of the present invention, by causing the driving portion to cause the distal end of the optical fiber to be oscillated along a spiral trajectory in accordance with the driving signal generated by the signal-generating portion, it is possible to scan the light emitted from the distal end of the optical fiber on an imaging subject along the spiral trajectory.

In this case, in the second period, the amplitude of the distal end of the optical fiber decreases to a minimum value in accordance with a decrease in the amplitude of the driving signal. The minimum value of the amplitude corresponds to a radius of a center region that is not irradiated with illumination light in the scanning trajectory, and the upper limit of the minimum value of the amplitude that is acceptable is 2% of the maximum value of the amplitude of the distal end of the optical fiber. In the following, the amplitude convergence rate is defined as:

Amplitude convergence rate=[minimum value of amplitude of distal end of optical fiber]/[maximum value of amplitude of distal end of optical fiber]×100.

By setting the frequency ratio fd/fr and the number of oscillations N2 so as to satisfy conditional expression (1) or (2), the amplitude convergence rate that is equal to or less than 2% is achieved while achieving quasi-resonance in the distal end of the optical fiber by means of the driving signal having a frequency that is close to the resonant frequency fr of the optical fiber, and thus, it is possible to reliably cause the oscillations of the distal end of the optical fiber to converge. When the amplitude convergence rate exceeds 2%, the center region that is not irradiated with the illumination light becomes excessively large, and thus, it becomes difficult to compensate for the information about the imaging subject in the center region by means of image processing or the like.

In the above-described first aspect, the signal-generating portion may generate the driving signal that satisfies conditional expression (3) below:

$$N2 \geq 60. \quad (3)$$

By doing so, in a practical range of the drive frequency fr with which it is possible to achieve quasi-resonance in the distal end of the optical fiber, it is possible to achieve an amplitude convergence rate that is equal to or less than 2%.

In the above-described first aspect, the signal-generating portion may generate the driving signal that satisfies conditional expression (4) or conditional expression (5) below:

$$fd/fr \geq 1.01; \quad (4)$$

$$fd/fr \leq 0.99. \quad (5)$$

By doing so, within the practical range of the number of oscillations N2, it is possible to achieve an amplitude convergence rate that is equal to or less than 2%.

A second aspect of the present invention is a light-scanning-apparatus control method in which light emitted from a distal end of an optical fiber is scanned on an imaging subject in a spiraling manner, the light-scanning-apparatus control method including: a signal-generating step of generating a driving signal that has a frequency different from a resonant frequency of the optical fiber and that is for causing the distal end of the optical fiber to undergo spiral oscillations; and a driving step of causing the distal end of the optical fiber to undergo spiral oscillations in accordance with the driving signal generated in the signal-generating step, wherein the signal-generating step generates the drive signal that includes, during one scanning period, a first period in which an amplitude gradually increases from substantially zero to a maximum value and a second period in which the amplitude gradually decreases from the maximum value to substantially zero, and that satisfies conditional expression (1) or conditional expression (2) below, where fr is the resonant frequency of the optical fiber; fd is the frequency of the driving signal; and N2 is the number of oscillations of the driving signal in the second period.

{Eq. 2}

$$2 \geq \frac{1}{N2^2} \cdot \frac{12}{\left(\frac{fd}{fr} - 0.999\right)^2} \left(\text{when } \frac{fd}{fr} > 1\right) \quad (1)$$

$$2 \geq \frac{1}{N2^2} \cdot \frac{12}{\left(1.001 - \frac{fd}{fr}\right)^2} \left(\text{when } \frac{fd}{fr} < 1\right) \quad (2)$$

REFERENCE SIGNS LIST 1 light-scanning apparatus
2 light-source portion
3 light-scanning portion
4 signal-generating portion
5 light-detecting portion
6 image-generating portion
7 control portion
8 irradiation optical fiber (optical fiber)
9 actuator
10 elastic portion
11A, 11B piezoelectric element
12A, 12B electrical cable
13 securing portion
14 light-receiving optical fiber
15 photodetector
16 A/D converter
17a, 17b scanning lens
20 endoscope
21 inserted portion
30 controller main unit
40 display
A imaging subject
B scanning trajectory

The invention claimed is:
1. A light-scanning apparatus comprising:
an optical fiber that emits light from a distal end thereof;
a signal generator that generates a driving signal that has a frequency different from a resonant frequency of the optical fiber and that is for causing the distal end of the optical fiber to undergo spiral oscillations; and an actuator that causes the distal end of the optical fiber to undergo spiral oscillations in accordance with the driving signal generated by the signal generator, wherein the signal generator generates the driving signal that includes, during one scanning period, a first period in which an amplitude gradually increases from substantially zero to a maximum value and a second period in which the amplitude gradually decreases from the maximum value to substantially zero, and that satisfies conditional expression (1) or conditional expression (2) below:

{Eq. 1}

$$2 \geq \frac{1}{N2^2} \cdot \frac{12}{\left(\frac{fd}{fr} - 0.999\right)^2} \left( \text{when } \frac{fd}{fr} > 1 \right) \quad (1)$$

$$2 \geq \frac{1}{N2^2} \cdot \frac{12}{\left(1.001 - \frac{fd}{fr}\right)^2} \left( \text{when } \frac{fd}{fr} < 1 \right) \quad (2)$$

where
fr is the resonant frequency of the optical fiber;
fd is the frequency of the driving signal; and
N2 is number of oscillations of the driving signal in the second period.

2. A light-scanning apparatus according to claim 1, wherein the signal generator generates the driving signal that satisfies conditional expression (3) below:

$$N2 \geq 60. \quad (3)$$

3. A light-scanning apparatus according to claim 1, wherein the signal generator generates the driving signal that satisfies conditional expression (4) below:

$$fd/fr \geq 1.01. \quad (4)$$

4. A light-scanning apparatus according to claim 1, wherein the signal generator generates the driving signal that satisfies conditional expression (5) below:

$$fd/fr \leq 0.99. \quad (5)$$

5. A light-scanning-apparatus control method in which light emitted from a distal end of an optical fiber is scanned on an imaging subject in a spiraling manner, the light-scanning-apparatus control method comprising:

generating a driving signal that has a frequency different from a resonant frequency of the optical fiber and that is for causing the distal end of the optical fiber to undergo spiral oscillations; and causing the distal end of the optical fiber to undergo spiral oscillations in accordance with the generated driving signal, wherein the generating of the driving signal generates the drive signal that includes, during one scanning period, a first period in which an amplitude gradually increases from substantially zero to a maximum value and a second period in which the amplitude gradually decreases from the maximum value to substantially zero, and that satisfies conditional expression (1) or conditional expression (2) below:

{Eq. 2}

$$2 \geq \frac{1}{N2^2} \cdot \frac{12}{\left(\frac{fd}{fr} - 0.999\right)^2} \left( \text{when } \frac{fd}{fr} > 1 \right) \quad (1)$$

$$2 \geq \frac{1}{N2^2} \cdot \frac{12}{\left(1.001 - \frac{fd}{fr}\right)^2} \left( \text{when } \frac{fd}{fr} < 1 \right) \quad (2)$$

where
fr is the resonant frequency of the optical fiber;
fd is the frequency of the driving signal; and
N2 is number of oscillations of the driving signal in the second period.

* * * * *